(12) United States Patent
Shimada et al.

(10) Patent No.: US 11,992,598 B2
(45) Date of Patent: May 28, 2024

(54) ADSORBING MATERIAL FOR SOLUBLE TUMOR NECROSIS FACTOR RECEPTOR

(71) Applicant: TORAY INDUSTRIES, INC., Tokyo (JP)

(72) Inventors: Kaoru Shimada, Otsu (JP); Megumi Nakanishi, Otsu (JP); Hiroshi Takahashi, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 490 days.

(21) Appl. No.: 17/442,247

(22) PCT Filed: Apr. 21, 2020

(86) PCT No.: PCT/JP2020/017183
§ 371 (c)(1),
(2) Date: Sep. 23, 2021

(87) PCT Pub. No.: WO2020/218291
PCT Pub. Date: Oct. 29, 2020

(65) Prior Publication Data
US 2022/0160946 A1    May 26, 2022

(30) Foreign Application Priority Data

Apr. 26, 2019 (JP) .................................. 2019-084877

(51) Int. Cl.
*B01J 20/26* (2006.01)
*A61M 1/36* (2006.01)

(52) U.S. Cl.
CPC ............ *A61M 1/3679* (2013.01); *B01J 20/26* (2013.01)

(58) Field of Classification Search
CPC .. A61M 1/3679; B01J 20/26; B01J 20/28004; B01J 20/28023; B01J 20/28069;
(Continued)

(56) References Cited

U.S. PATENT DOCUMENTS

| 5,633,290 A | 5/1997 | Frechet et al. |
| 2005/0036979 A1 | 2/2005 | Metzger et al. |

(Continued)

FOREIGN PATENT DOCUMENTS

| JP | 5-131028 A | 5/1993 |
| JP | 5-345022 A | 12/1993 |

(Continued)

OTHER PUBLICATIONS

Extended European Search Report for European Application No. 20795553.5, dated Dec. 19, 2022.
(Continued)

*Primary Examiner* — Thuan D Dang
(74) *Attorney, Agent, or Firm* — Birch, Stewart, Kolasch & Birch, LLP (57) ABSTRACT

The present invention aims to provide a material for adsorbing soluble tumor necrosis factor receptors with high efficiency. The present invention provides an adsorbing material for soluble tumor necrosis factor receptors, which includes a superficially porous water-insoluble polymeric material, wherein the pore size distribution curve for the surface of the water-insoluble polymeric material, which is derived from a distribution of melting points determined by differential scanning calorimeter, shows the peak radius in the range of 1 to 80 nm, and the water-insoluble polymeric material has a zeta potential at pH 7.4 of −15 to 15 mV, and the water-insoluble polymeric material is in fiber, particle, or film form.

8 Claims, 4 Drawing Sheets

(58) Field of Classification Search
CPC .............. B01J 20/28078; B01J 20/321; B01J 20/3219; B01J 20/3248; B01J 20/327; B01J 20/3272
See application file for complete search history.

(56) References Cited

U.S. PATENT DOCUMENTS

| | | | |
|---|---|---|---|
| 2009/0275874 A1 | 11/2009 | Shimagaki et al. | |
| 2010/0025335 A1 | 2/2010 | Shimaki | |
| 2013/0112605 A1* | 5/2013 | Wyndham | B01J 20/285 252/62.51 C |

FOREIGN PATENT DOCUMENTS

| | | |
|---|---|---|
| JP | 8-502534 A | 3/1996 |
| JP | 2004-358256 A | 12/2004 |

OTHER PUBLICATIONS

Ishikiriyama et al., "Pore Size Distribution (PSD) Measurements of Silica Gels by Means of Differential Scanning Calorimetry", Journal of Colloid and Interface Science, vol. 171, 1995, pp. 92-102.
Author Unknown, "Tosoh Separation Report," No. 113, p. 1 (16 pages total), with partial English translation.
Kasakura et al., "All about Cytokines and Chemokines," Nihon Igakkan, 3rd Edition, 2004, pp. 279-298 (23 pages total), with partial English translation.
Yoshida et al., "Chemical Engineering and Artificial Organs," Kyoritsu Shuppan, 2nd Edition, 1997, p. 187 (3 pages total), with partial English translation.
International Search Report, issued in PCT/JP2020/017183, PCT/ISA/210, dated Jul. 14, 2020.
Written Opinion of the International Searching Authority, issued in PCT/JP2020/017183, PCT/ISA/237, dated Jul. 14, 2020.

* cited by examiner

Longitudinal direction

Fig.4

Longitudinal direction

ADSORBING MATERIAL FOR SOLUBLE TUMOR NECROSIS FACTOR RECEPTOR

TECHNICAL FIELD

The present invention relates to an adsorbing material for soluble tumor necrosis factor receptors.

BACKGROUND ART

Tumor necrosis factor, a cytokine present in blood, is a substance that plays important roles in immunological functions, such as cellular cytotoxicity and antiviral activity. It is known that tumor necrosis factor receptors, which are the receptors of tumor necrosis factor, usually reside in the cell membrane, and that enzymatic cleavage of the extracellular domains of tumor necrosis factor receptors by tumor necrosis factor-α convertase results in release of soluble tumor necrosis factor receptors, such as soluble tumor necrosis factor receptor 1 (hereinafter referred to as sTNFR1) and soluble tumor necrosis factor receptor 2 (hereinafter referred to as sTNFR2), into blood and urine.

Soluble tumor necrosis factor receptors are known to bind to tumor necrosis factor and to repress the activity of tumor necrosis factor and are also known to be biomarkers identified in blood in association with conditions such as general inflammation, sepsis, acute respiratory distress syndrome, hepatitis C, cancer, leukemia, atrial fibrillation, heart failure, cachexy, and autoimmune diseases, and studies are conducted to understand, for example, the physiological activities of soluble tumor necrosis factor receptors.

For example, Non-Patent Document 1 reports that, based on the repression of tumor necrosis factor activity by binding of soluble tumor necrosis factor receptors to tumor necrosis factor, removal of free soluble tumor necrosis factor receptors from blood could increase the antitumor and antimicrobial activities of tumor necrosis factor.

Patent Document 1 discloses a method and a system for removing sTNFR1, sTNFR2, and soluble interleukin 2 receptor (hereinafter referred to as sAL2R) from blood or the like of patients (for example, patients with cancer) and also disclosed a material for adsorbing sTNFR1, sTNFR2, and sAL2R, on which, for example, antibodies against those receptors are immobilized.

Patent Document 2 discloses an adsorbing material for soluble tumor necrosis factor receptors, in which a compound with a log P value (P represents an octanol-water partition coefficient) of not less than 2.5 (for example, hexadecylamine) is immobilized on a water-insoluble carrier.

On the other hand, Patent Document 3 discloses an adsorber which characteristically includes a water-insoluble material for adsorbing or removing leukocytes and cytokines from whole-blood dispersions. It is considered preferable that the water-insoluble material has a porosity of less than 30% for pores with a pore size of not less than 1 pin and not more than 100 μm, linked with hydrophilic amine residues, and has a fiber diameter of not less than 5 μm and not more than 20 μm.

Patent Document 4 discloses an adsorbing material for use in blood treatment, wherein the adsorbing material for use in blood treatment has excellent wettability with blood and causes no increase in kinin levels during the treatment of blood or plasma, and wherein the adsorbing material is a water-insoluble carrier composed of a polymer with a molecular weight exclusion limit of not less than 50,000 and not more than 10,000,000, which carrier has functional groups with binding activities to unnecessary substances on the surface thereof, and has a total surface charge of not less than −30 μeq/g.

Patent Document 5 discloses an adsorbing material for granulocytes, monocytes, and cytokines in blood. It is considered preferable that the adsorbing material has a surface zeta potential of not less than −20 mV and not more than 10 mV, and that, in cases where the adsorbing material is in fiber form, the adsorbing material has a fiber diameter of not less than 4 μm and not more than 20 sm from the viewpoint of practical use.

Patent Document 6 discloses an adsorbing material in which the amount of amino and amide groups incorporated in a ligand is regulated to achieve adsorption of cytokines and activated leukocyte-activated platelet complexes.

Patent Document 7 discloses an adsorbing material in which the developed length ratio and the roughness on the surface of the material are regulated to achieve adsorption of activated leukocyte-activated platelet complexes.

Patent Document 8 discloses an adsorbing material in which optimization of fiber diameter and porosity prevents pressure loss from occurring in an adsorption column.

PRIOR ART DOCUMENTS

Patent Documents

Patent Document 1: JP 2008-511340 T
Patent Document 2: JP 2009-178523 A
Patent Document 3: JP 2007-202634 A
Patent Document 4: JP H6-007430 A
Patent Document 5: JP 2006-312804 A
Patent Document 6: WO 2018/047929
Patent Document 7: WO 2018/225764
Patent Document 8: WO 2020/026698

Non-Patent Documents

Non-Patent Document 1: Shinpei Kasakura, el al., All about Cytokines and Chemokines. Third Edition. Nihon Igakkan, 2004, p. 279-298.
Non-Patent Document 2: Tosoh Separation Report, No. 113, p. 1.
Non-Patent Document 3: Fumitake Yoshida, el al., Chemical Engineering and Artificial Organs, Second Edition. Kyoritsu Shuppan, 1997, p. 187.

SUMMARY OF THE INVENTION

Problems to be Solved by the Invention

In Patent Document 2, a water-insoluble porous carrier having a molecular weight exclusion limit of not less than 20,000 Da and less than 100,000 Da is considered preferable as the water-insoluble carrier from the viewpoint of adsorption capacity and selectivity. However, the water-insoluble porous carrier is considered not suitable as an adsorbing material for soluble tumor necrosis factor receptors because the upper limit of the fractionation range, 100,000 Da, corresponds to a pore radius as small as 0.5 nm, as calculated by the following procedure, and soluble tumor necrosis factor receptors are estimated to have a radius as large as 2 nm. In this respect, the pore radius in the material with a molecular weight exclusion limit of 100.000 Da was calculated on the basis of the relationship established between pore sizes and molecular weight exclusion limits of porous materials, on the surface of which antibodies are immobilized (Non-Patent Document 2). The radii of soluble tumor necrosis factor receptors were calculated from the molecular weights of the soluble tumor necrosis factor receptors, each having about 20,000 Da, on the basis of the relationship between molecular weight and Stokes radius (Non-Patent Document 3).

Additionally, Patent Document 2 describes that the water-insoluble carrier with a porous structure prefers to have a fully porous structure rather than a superficially porous structure, but the water-insoluble carrier with a fully porous structure could have a higher risk of fracture due to a lower tensile strength and therefore require laborious efforts to be made for quality control in terms of safety. In Examples, only n-hexadecylamine ($CH_3(CH_2)_{15}NH_2$; $\Sigma f=7.22$) is indicated as a compound immobilized onto the carrier and no polyamine derivatives are disclosed. Moreover, no disclosure or suggestion is made with respect to, for example, the charge near the surface of the adsorbing material.

Patent Document 3 describes that pores penetrate through the material to form flow channels for blood cells and the pores include, for example, voids generated between fibers. That is. Patent Document 3 does not refer to pores formed on the surface of the material are not included. Moreover, it is considered preferable that the material has a porosity of less than 30% for pores with a pore size of not less than 1 μm and not more than 100 μm and preferably contains more pores with a pore size of not less than 100 μm, but nanoscale pores formed on the surface of the material are not described. Tumor necrosis factor-alpha is described as an illustrative example of cytokine, but no disclosure or suggestion is made with respect to soluble tumor necrosis factor receptors which are different from cytokines and blood cell components.

Patent Document 4 describes a design for a material with a molecular weight exclusion limit defined from the viewpoint of binding to plasma proteins and to other various components in plasma and with a total surface charge defined from the viewpoint of regulation of kinin generation, but does not disclose or suggest soluble tumor necrosis factor receptors and the relations between the receptors and the surface conditions of the material.

Patent Document 5 does not disclose or suggest soluble tumor necrosis factor receptors which are different from cytokines and blood cell components, and the relations between the receptors and the surface conditions of the material. As disclosed in Examples, the adsorption rate of blood cell components such as neutrophils and monocytes is greatly reduced in cases where the adsorbing material has a fiber diameter in the range of 10 μm to 17 μm. Thus, it is considered appropriate that the adsorbing material described in Patent Document 5 has a fiber diameter as long as several micrometers in cases where the adsorbing material is used to remove cytokines and blood cell components.

Patent Documents 6 to 8 do not disclose or suggest soluble tumor necrosis factor receptors and the relations between the receptors and the surface conditions of the materials, and do not disclose a design for a material suitable for adsorption of soluble tumor necrosis factor receptors.

Thus, an object of the present invention is to provide a material for efficient adsorption of soluble tumor necrosis factor receptors.

Means for Solving the Problem

The inventors had thought that it was important to design the surface conditions of a material consistent with the properties of soluble tumor necrosis factor receptors in order to increase the adsorption efficiency for soluble tumor necrosis factor receptors. As a result of intensive study, the inventors consequently found that, among the surface conditions of the material, the peak radius and zeta potential of pores on the material surface are important, and that efficient adsorption of soluble tumor necrosis factor receptors can be achieved by controlling the peak radius and the zeta potential within appropriate ranges, thereby completing the present invention.

That is, the present invention encompasses the following items [1] to [8].

[1] An adsorbing material for soluble tumor necrosis factor receptors, comprising a superficially porous water-insoluble polymeric material,
wherein the pore size distribution curve for the surface of the water-insoluble polymeric material, which is derived from a distribution of melting points determined by differential scanning calorimeter, shows the peak radius in the range of 1 to 80 nm;
the water-insoluble polymeric material has a zeta potential at pH 7.4 of −15 to 15 mV; and
the water-insoluble polymeric material is in fiber, particle, or film form.

[2] The adsorbing material according to [1], wherein the water-insoluble polymeric material is in fiber form with a fiber diameter of 25 to 65 μm or in particle form with a particle size of 25 to 65 μm.

[3] The adsorbing material according to [1] or [2], wherein the ratio B defined by the following equation (1) is not less than 10% and not more than 90%, where A1 and A2 represent the areas of non-porous and porous regions, respectively, in a cross section passing through the center of the water-insoluble polymeric material and perpendicular to the longitudinal direction, and B represents the ratio of the area of the non-porous region in the cross section:

$$B=A1/(A1+A2)\times100 \qquad \text{Equation (1)}.$$

[4] The adsorbing material according to any one of [1] to [3], wherein the peak radius is in the range of 1 to 30 nm.
[5] The adsorbing material according to any one of [1] to [4], wherein the water-insoluble polymeric material has a pore volume of 0.6 to 1.2 $cm^3/g$.
[6] The adsorbing material according to any one of [1] to [5], wherein an amino group-containing ligand is bound to the surface of the water-insoluble polymeric material.
[7] The adsorbing material according to any one of [1] to [6], wherein the water-insoluble polymeric material contains polystyrene, polyethylene, or polypropylene as a main component.
[8] An adsorption column comprising the adsorbing material according to any one of [1] to [7].

Effect of the Invention

An adsorbing material according to the present invention can remove soluble tumor necrosis factor receptors with high efficiency and is useful as a carrier for use in extracorporeal circulation.

MODE FOR CARRYING OUT THE INVENTION

The present invention will be described below in detail.

The adsorbing material for soluble tumor necrosis factor receptors of the present invention comprises a superficially porous water-insoluble polymeric material, wherein the pore size distribution curve for the surface of the water-insoluble polymeric material, which is derived from a distribution of melting points determined by differential scanning calorimeter, shows the peak radius in the range of 1 to 80 nm, and the water-insoluble polymeric material has a zeta potential at pH 7.4 of −15 to 15 mV, and the water-insoluble polymeric material is in fiber, particle, or film form.

The term "soluble tumor necrosis factor receptors" refers to tumor necrosis factor receptors which are solubilized and released into blood and urine, and the soluble tumor necrosis factor receptors (sTNFRs) means two types of soluble tumor necrosis factor receptor 1 (sTNFR1) and soluble tumor necrosis factor receptor 2 (sTNFR2). The adsorbing material of the present invention is a material for adsorbing both sTNFR1 and sTNFR2.

The term "adsorbing material" means a material with properties that can adsorb a specific substance and can prevent easy release of the adsorbed substance from the material. The term means, for example, a material for adsorbing based on intermolecular forces, such as electrostatic interaction, hydrophobic interaction, hydrogen bonding, and van der Waals force, but the principle of adsorption is not specifically limited thereto.

The term "superficially porous" refers to a condition of a material in which pores are present on the surface of the material but do not penetrate through the material. It is thought that superficially porous materials are more excellent than fully porous materials, in which pores are present throughout the materials, with respect to fast mass transport and to ability to retain strength.

The term "water-insoluble polymeric material" refers to a polymeric material insoluble in water. In this respect, the phrase "insoluble in water" means that the percent change in the dry weight of a water-insoluble polymeric material before and after soaking in water is not more than 1% by weight. The change in dry weight is expressed by the ratio of the dry weight of the water-insoluble polymeric material after soaking in water to that before soaking in water, where the water-insoluble polymeric material is soaked in an amount of water equivalent to 9 times the dry weight of the water-insoluble polymeric material at 37° C. for 1 hour, picked up with, for example, forceps, and dried under vacuum at a temperature of not higher than 50° C. until the water-insoluble polymeric material reaches a constant weight, and the dry weight of the remaining solids is then weighed to determine the dry weight of the water-insoluble polymeric material after soaking in water. Any polymeric material that has not been made insoluble in water is undesirable for safety reasons because such a polymeric material has a risk of dissolving off a large portion of the polymeric material during practical use.

The material used for the water-insoluble polymeric material is not limited in terms of specific chemical and physical structures, provided that the material is insoluble in water and is composed of a polymer. Examples of the material include polymeric materials with repeat units containing a functional group, such as aryl or hydroxyl group, that is reactive with carbocations, including, for example, synthetic polymers, such as aromatic vinyl polymer, polyester, polysulfone, polyether sulfone, polystyrene, and polyvinyl alcohol; or naturally occurring polymers, such as cellulose, collagen, chitin, chitosan, and dextran. These polymers may be used as homopolymers or copolymers, or may be used as polymer blends or alloys. The material, particularly for blood purification, preferably contains one or more polymers selected from the group consisting of aromatic vinyl polymers, polyethylene terephthalate, polybutylene terephthalate, polystyrene, polysulfones, and polyether sulfones, which are polymeric materials containing no hydroxyl groups, and more preferably contains polystyrene, polyethylene, or polypropylene as a main component. Among others, polystyrene is particularly preferable as a main component since the number of aromatic rings per unit weight is large and various functional groups or reactive functional groups can be easily incorporated into the material by, for example, the Friedel-Crafts reaction. In this respect, the term "main component" means a component which is the most abundant among the components constituting the water-insoluble polymeric material. In cases where the water-insoluble polymeric material is in a form of sea-island type composite fiber, the water-insoluble polymeric material is composed of, for example, a sea component that is a polystyrene or an alloy prepared by kneading polystyrene and a polypropylene and an island component containing either or both of polypropylene and polyethylene. Such water-insoluble polymeric materials can be commercially available or can be produced by any known method.

Additionally, the water-insoluble polymeric material includes not only non-surface-treated water-insoluble polymeric materials but also surface-treated water-insoluble polymeric materials, such as water-insoluble polymeric materials modified by, for example, ligand incorporation reaction.

The "differential scanning calorimeter" is also known as differential scanning calorimetry (hereinafter referred to also as DSC) and is recently used as an apparatus to analyze a pore size distribution in a wet sample. The principle of pore size measurement by DSC is based on the melting point depression of water confined in nano-scale pores, relative to the normal melting point of bulk ice (melting point: 0° C.), and this phenomenon can be used to provide a pore size distribution from a distribution of melting points in a DSC curve. Specifically, the pore size distribution can be calculated from the distribution of melting points in the DSC curve according to the method described in Ishikiriyama el al. (Journal of Colloid and Interface Science, 1995, 171: 92-102). The analysis of pore size distribution may not be applicable to a sample containing any water-soluble impurity because the presence of such an impurity causes a melting point depression of water. Therefore, a sample applied to the analysis is required to contain no water-soluble impurities. The conditions for the DSC analysis are as described below.

| | |
|---|---|
| DSC apparatus: | DSC Q100 manufactured by TA Instruments; |
| Temperature measurement range: | from about −55° C. to 5° C.; |
| Temperature rising rate: | 0.3° C./min; |
| Sample weight: | about 6 mg (an indicated DSC curve is normalized to 5 mg); |
| Sample container: | Sealing-type aluminum sample container; |
| Temperature and heat flow calibration: | Pure water (melting point: 0.0° C.; heat of fusion: 79.7 cal/g); |
| Sample pretreatment: | excess water (bulk water) attached on the surface removed. |

Figure 1:
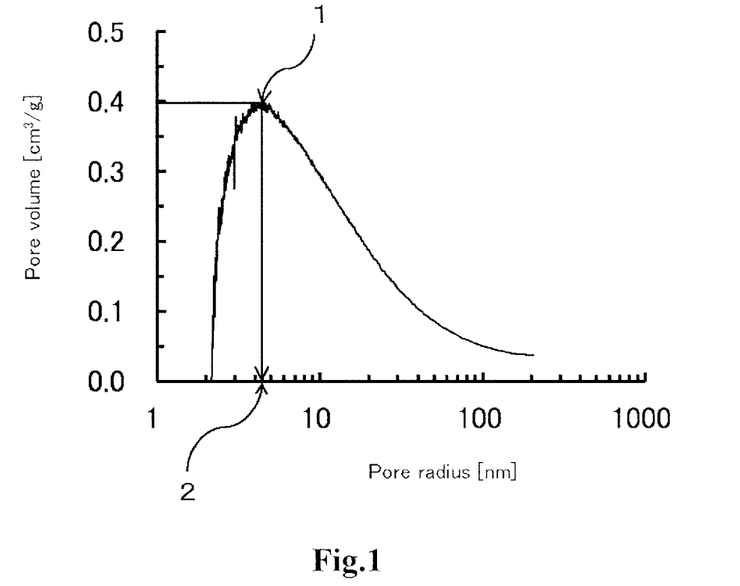
FIG. 1 shows a diagram for explaining the peak radius in a pore size distribution curve.

The peak radius in a pore size distribution curve means the pore radius at which the pore volume per wet weight of a water-insoluble polymeric material reaches the maximum in the pore size distribution curve, which is prepared by plotting a distribution of pore sizes measured by the above-described DSC, as shown in FIG. 1 (horizontal axis: pore radius; vertical axis: pore volume per wet weight of the water-insoluble polymeric material).

Importantly, the sizes of pores formed on the surface of a water-insoluble polymeric material is properly controlled with respect to the sizes of sTNFRs for increasing the efficiency of adsorbing sTNFRs. As a result of investigation based on an idea that efficient confinement of sTNFRs within pores in a water-insoluble polymeric material would lead to an increase in adsorption efficiency, the inventors found that the adsorption efficiency for sTNFRs could be increased by formation of pores of appropriate size at high density on the surface of the material.

The peak radius of pores on the surface of the water-insoluble polymeric material should be not less than 1 nm from the viewpoint of increasing the amount and easy invasion of adsorbed sTNFRs, and be not more than 80 nm from the viewpoint of achieving the selective adsorption of sTNFRs. That is, the peak radius of pores on the surface of the water-insoluble polymeric material is necessarily in the range of 1 to 80 nm, preferably in the range of 1 to 30 nm, more preferably in the range of 1 to 20 nm, still more preferably in the range of 3 to 20 nm.

The pores on the surface of the water-insoluble polymeric material can be formed by, for example, hydrophilizing the surface of the water-insoluble polymeric material to allow the surface to expand. For example, the surface of the water-insoluble polymeric material can be hydrophilized to allow the surface to expand and to form pores on the surface by immobilizing an acidic or basic functional group-containing ligand on the surface. In this respect, nitrobenzene is suitable for use as a solvent used in the above ligand immobilization reaction on the surface of the water-insoluble polymeric material. Moreover, the surface of the water-insoluble polymeric material can also be hydrophilized to allow the surface to expand and then soaked in alcohol to form pores on the surface. Examples of the alcohol include methanol, ethanol, and isopropyl alcohol. In addition, the size of pores can be controlled by temperature during the soaking in alcohol, and the temperature is preferably from 20 to 60° C., more preferably from 30 to 50° C. from the viewpoint of increasing the capacity of adsorption. Moreover, the size of pores can also be controlled by the length of time of soaking in alcohol, and the length of soaking time is preferably from 5 to 60 minutes, more preferably from 20 to 40 minutes, from the viewpoint of increasing the capacity of adsorption. In Examples of the above Patent Documents 6 to 8, the temperature and length of time of soaking in methanol are not mentioned in connection with the production of chloroacetamidomethylated knitted fabrics.

The peak radius of pores on the surface of the water-insoluble polymeric material can be controlled by the type of polymer and/or the conditions for blending or alloying polymers in the water-insoluble polymeric material. For example, the above peak radius of pores can be controlled by changing the ratio of polystyrene and polypropylene in an alloy.

The term "zeta potential" refers to the difference between the potential of the slipping plane and the potential at a position far enough from the interfacial plane in the electrical double layer. The zeta potential in this application means a value determined using electrophoresis at pH 7.4 and a temperature of 20 t 5° C.

Non-surface-treated water-insoluble polymeric materials made of polystyrene, polyethylene, and/or polypropylene have a minus value of zeta potential, generally a zeta potential of around −30 mV. Methods to control the zeta potential at −15 mV or higher include an immobilization method of a ligand containing a particular functional group (for example, an acidic or basic functional group) on the surface of the water-insoluble polymeric material is discussed as a. It was found as a result of the investigation that a zeta potential of not less than −15 mV would lead to an increased electrostatic interaction between sTNFRs and the surface of the water-insoluble polymeric material, while a zeta potential of not less than 15 mV may cause adverse effects on erythrocytes. Thus, the zeta potential is required to be from −15 to 15 mV and is preferably from −10 to 12 mV, more preferably from −4 to 10 mV. The preferred aspects of the peak radius and zeta potential as described above are available in any combination.

As the form of the water-insoluble polymeric material, a fiber, a particle, or a film is suitable for use. A fiber form, particularly a form of sea-island type composite fiber, is preferable for use as an adsorbing material because the fiber form has a large specific surface area and is sufficiently flexible and deformable, and easy handling. Among others, a form of sea-island type composite fiber that is composed of polystyrene as a sea component and polypropylene as an island component is preferable. Moreover, from the viewpoint of packing of the adsorbing material prior to use and of uniform flow pass of liquids, a form of woven, non-woven, or knitted fabric is more preferable among those fiber forms. The adsorbing material for soluble tumor necrosis factor receptors can comprise, at least in part, a water-insoluble polymeric material and may be composed of a water-insoluble polymeric material alone or of a water-insoluble polymeric material to which an appropriate reinforcement material is immobilized or combined. The immobilization or combination process may be carried out before or after a forming process.

The term "fiber diameter" refers to an average value of diameters determined by randomly collecting 10 small samples of fibers, which constitute a woven, non-woven, or knitted fabric of the water-insoluble polymeric material, taking a picture of each sample with a scanning electron microscope, and measuring the diameters of the fiber at 10 positions in each picture (a total 100 fibers). In this respect, each fiber is observed at a magnification that allows the diameter of the fiber to account for 30 to 80% of the long side length of a picture. Moreover, in the case of a multi-filament composed of a bundle of fibers, the diameter of each single fiber constituting the multifilament is considered as the fiber diameter.

The water-insoluble polymeric material in fiber form preferably has a fiber diameter of not less than 25 µm, more preferably not less than 30 µm, from the viewpoint of preventing platelet adsorption, which is required for arrest of bleeding. Moreover, the fiber preferably has a fiber diameter of not more than 65 µm, more preferably not more than 50 µm, from the viewpoint of securing fibers with a sufficient specific surface area for adsorption of sTNFRs. That is, the fiber preferably has a fiber diameter in the range of 25 to 65 µm, more preferably in the range of 30 to 50 µm. In those preferred ranges, either of the lower limits may be combined with either of the upper limits.

The term "particle size" refers to an average value of diameters determined by randomly collecting 10 small samples of, for example, beads, which constitute particles of the water-insoluble polymeric material, taking a picture of each sample with a scanning electron microscope, and measuring the diameters of particles at 10 positions in each picture (a total 100 particles). In this respect, each particle is observed at a magnification that allows the diameter of the particle to account for 30 to 80% of the long side length of a picture.

The water-insoluble polymeric material in particle form preferably has a particle size of not less than 25 µm, more preferably not less than 30 µm, from the viewpoint of preventing platelet adsorption. Moreover, the particle preferably has a particle size of not more than 65 µm, more preferably not more than 50 µm, from the viewpoint of securing particles with a sufficient specific surface area for adsorption of sTNFRs. That is, the particle preferably has a particle size in the range of 25 to 65 µm, more preferably in the range of 30 to 50 µm. In those preferred ranges, either of the lower limits may be combined with either of the upper limits. Additionally, particles with a narrow particle size distribution are more preferable because, for example, particles with such a size distribution cause no increased pressure loss.

In cases where a cross section passing through the center of a water-insoluble polymeric material and perpendicular to the longitudinal direction (FIGS. 2 to 7) includes the area of a non-porous region A1 and the area of a porous region A2, the ratio B of the area of the non-porous region can be calculated according to the following equation (1). In this method, each water-insoluble polymeric material is pretreated by ruthenium tetroxide staining, followed by cryo-ultramicrotomy, and cross sections each passing through the center of the material and perpendicular to the longitudinal direction are randomly observed at a magnification of 8,000 times with a transmission electron microscope EM-1400 Plus (manufactured by JEOL Ltd.) at an accelerated voltage of 100 kV, and 100 cross-sectional images are acquired. In the acquired cross-sectional images, the areas of the non-porous region A1 and porous region A2 can be distinguished based on the pores on the surface of the material detected in the cross-sectional images. The area of the non-porous region A1 is defined as the sum of the area of region where pores with a pore size of less than 10 nm are present and the area of region where no pores are present, while the area of the porous region A2 is defined as the area of a region where pores with a pore size of not less than 10 nm are present. In cases where two or more water-insoluble polymer components are visible in a cross section, the boundaries between those components (for example, a sea component and an island component) in the cross section should be used as the boundaries between the areas of the non-porous region A1 and porous region A2. In this case, the sum of the area of a component where pores with a pore size of less than 10 nm are present and the area of a component where no pores are present is calculated as the area of the non-porous region A1, and the area of a component where pores with a pore size of not less than 10 nm are present is calculated as the area of the porous region A2. The areas can be calculated using image editing software (Photoshop Elements, 14.0; manufactured by Adobe Inc.).

Figure 2:
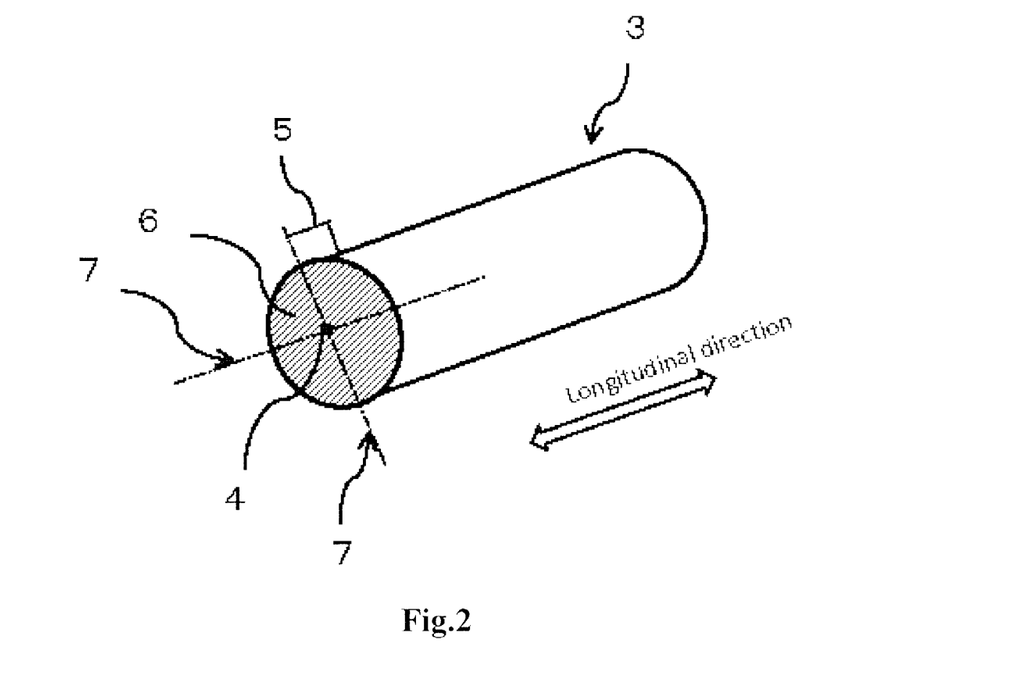
FIG. 2 shows a cross section of an example of an adsorbing material according to the present invention (in fiber form) cut through the center and perpendicular to the longitudinal direction.
Figure 3:
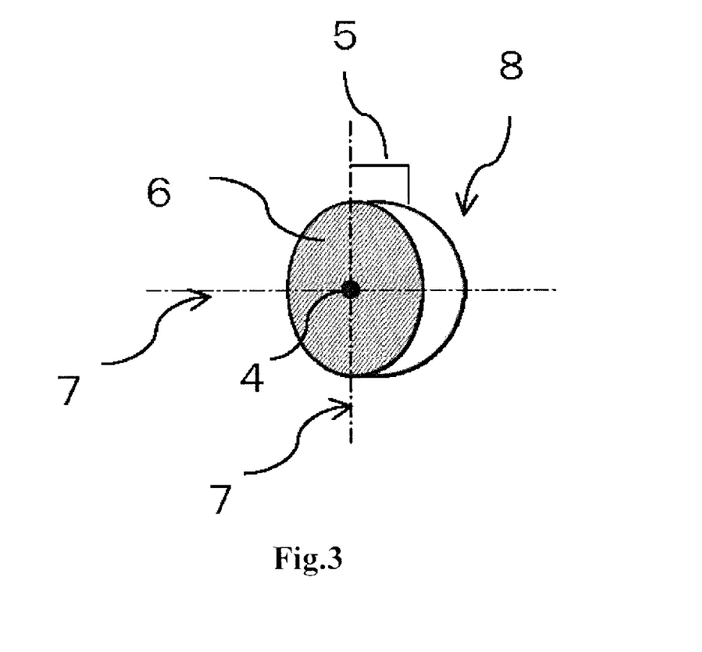
FIG. 3 shows a cross section of an example of an adsorbing material according to the present invention (in spherical particle form) cut through the center and perpendicular to the longitudinal direction.
Figure 4:
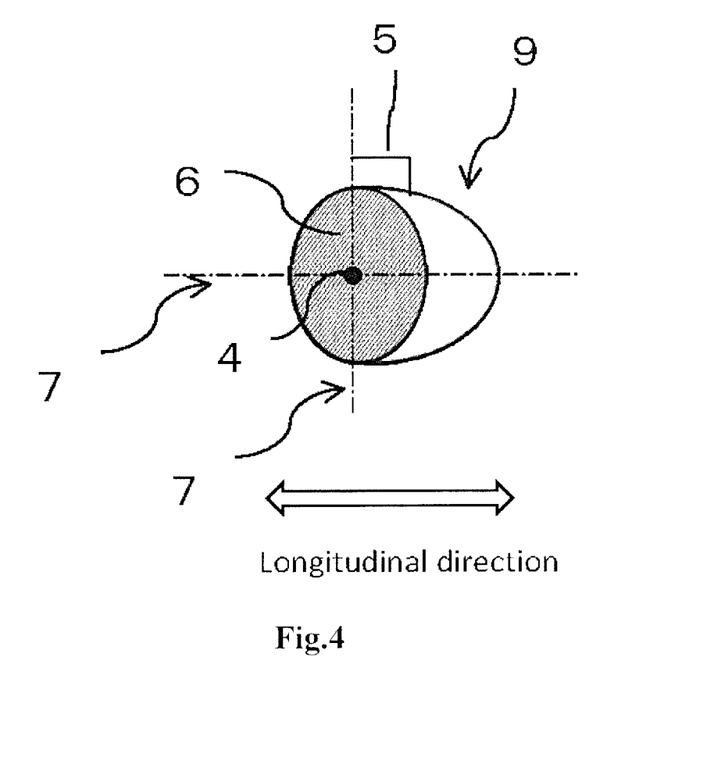
FIG. 4 shows a cross section of an example of an adsorbing material according to the present invention (in ellipsoidal particle form) cut through the center and perpendicular to the longitudinal direction.
Figure 5:
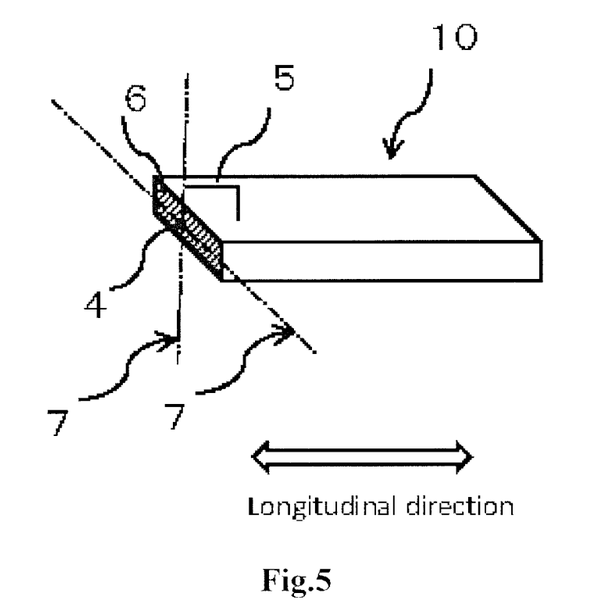
FIG. 5 shows a cross section of an example of an adsorbing material according to the present invention (in film form) cut through the center and perpendicular to the longitudinal direction.
Figure 6:
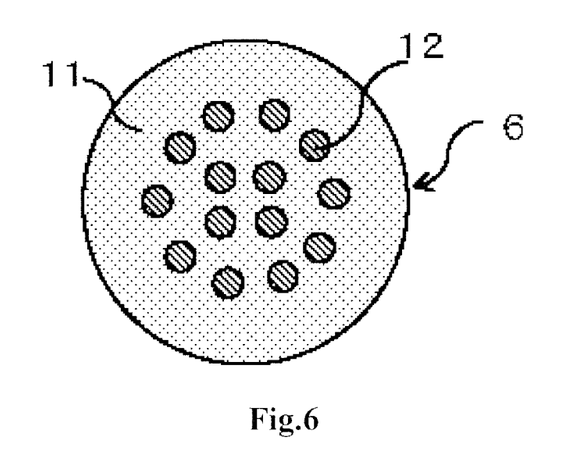
FIG. 6 shows a cross section of an example of an adsorbing material according to the present invention (in fiber or particle form) cut through the center and perpendicular to the longitudinal direction, for explaining the area A2 of porous region and the area A1 of non-porous region.
Figure 7:
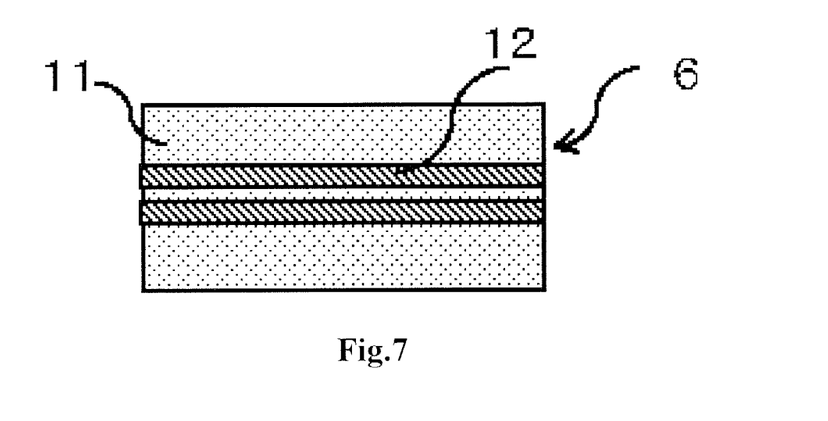
FIG. 7 shows a cross section of an example of an adsorbing material according to the present invention (in film form) cut through the center and perpendicular to the longitudinal direction, for explaining the area A2 of porous region and the area A1 of non-porous region.

FIG. 2 shows as an example a cross section passing through the center of a water-insoluble polymeric material in fiber form and perpendicular to the longitudinal direction. The center is the intersection (4) of two centerlines (7) on the cross section perpendicular to the longitudinal direction. FIG. 3, 4, or 5 shows as an example a cross section passing through the center of a water-insoluble polymeric material in spherical particle, ellipsoidal particle, or film form respectively, and perpendicular to the longitudinal direction, similarly to that shown in FIG. 2. Since the concept of longitudinal direction is not applicable to spherical particles as shown in FIG. 3, any cross section passing through the center of each spherical particle is accepted. Examples of the obtained cross sections applied to image analysis are shown in FIG. 6 and FIG. 7. The ratio B of the area of the non-porous region defined by the following equation (1) can be determined where A1 refers to the sum of the areas of non-porous regions (12) where pores with a pore size of less than 10 nm are observed (including a region(s) with no pores) and A2 refers to the sum of the areas of porous regions (11) where pore with a pore size of not less than 10 nm are observed:

$$B = A1/(A1+A2) \times 100 \qquad \text{Equation (1).}$$

The ratio B of the area of the non-porous region in the above cross section is preferably not less than 10% because a water-insoluble polymeric material with a too small ratio B will reduce strength of a material and be unable to retain the form of an adsorbing material. On the other hand, the ratio B of the area of the non-porous region is preferably not more than 90% because a water-insoluble polymeric material with a too large ratio B will be unable to exhibit an adsorption capacity. That is, the ratio B of the area of the non-porous region is preferably in the range of 10 to 90%, more preferably in the range of 20 to 80%, still more preferably in the range of 30 to 70%. In those preferred ranges, any of the lower limits may be combined with any of the upper limits.

The term "pore volume" means the volume of pores per 1 g of a water-insoluble polymeric material, which is determined from a distribution of melting points measured by DSC. A method of measuring pore volume by means of DSC is similar to the above pore-size measurement method, and the pore volume can be calculated from the distribution of melting peaks in the DSC curve according to the method described in Ishikiriyama et al. (Journal of Colloid and Interface Science, 1995, 171:92-102).

The pore volume is preferably not less than 0.06 $cm^3/g$ because a water-insoluble polymeric material with a too small pore volume will be unable to improve adsorption capacity sufficiently. On the other hand, the pore volume is preferably not more than 1.2 $cm^3/g$ because a water-insoluble polymeric material with a too large pore volume will be unable to have properties for selective adsorption of sTNFRs. That is, the pore volume of the water-insoluble polymeric material is preferably in the range of 0.06 to 1.2 cm$^3$/g, more preferably in the range of 0.3 to 1.2 cm$^3$/g. Furthermore, a water-insoluble polymeric material with a pore volume of 0.6 to 1.2 cm$^3$/g can be expected to have 80 or more percent of adsorption rate of soluble tumor necrosis factor receptors at 2 hours after the start of extracorporeal circulation, and such a water-insoluble polymeric material can complete the treatment within 4 hours, which allows patients to receive outpatient care, and is therefore believed to reduce burden on the patients. In this respect, the preferred aspects of the pore volume of the above water-insoluble polymeric material and the fiber diameter or particle size of the above water-insoluble polymeric material are available in any combination.

In the above water-insoluble polymeric material, a ligand may be bound to the surface. In this specification, the term "ligand" means a compound bound to the surface of the water-insoluble polymeric material, and the chemical structure of the compound is not specifically limited as long as the compound contains an acidic or basic functional group. Examples of the compound include compounds with a sulfonate or carboxyl group, which is an acidic functional group (an anionic functional group), and compounds with an amino group, which is a basic functional group (a cationic functional group). In this embodiment, a compound with a basic functional group, particularly a compound with an amino group, is preferred as the ligand. The above functional group may be a combination of the same or different functional groups. The ligand may further contain a neutral functional group as long as the ligand contains an acidic or basic functional group as described above. Examples of the ligand include an acidic or basic functional group-containing compound to which a neutral functional group is further bound (for example, para (p)-chlorophenyl group-bound tetraethylenepentamine), where the neutral functional group is, for example, an alkyl group such as methyl or ethyl group, or an aryl group such as a phenyl group, an alkyl-substituted phenyl group (for example, para (p)-methylphenyl group, meta (m)-methylphenyl group, ortho (o)-methylphenyl group, para (p)-ethylphenyl group, meta (m)-ethylphenyl group, or ortho (o)-ethylphenyl group), or a halogen atom-substituted phenyl group (for example, para (p)-fluorophenyl group, meta (m)-fluorophenyl group, ortho (o)-fluorophenyl group, para (p)-chlorophenyl group, meta (m)-chlorophenyl group, or ortho (o)-chlorophenyl group). In this case, the neutral functional group may be bound to the ligand, either directly or via a spacer (the spacer involved in such binding is also called spacer 1). Examples of the spacer 1 include a urea bond, an amide bond, and a urethane bond.

Examples of the "amino group" include amino groups derived from primary amines, such as methylamine, ethylamine, propylamine, butylamine, pentylamine, hexylamine, heptylamine, octylamine, and dodecylamine; amino groups derived from secondary amines, such as methylhexylamine, diphenylmethylamine, and dimethylamine; amino groups derived from amines with an unsaturated alkyl chain, such as allyl amines; amino groups derived from tertiary amines, such as trimethylamine, triethylamine, dimethylethylamine, phenyldimethylamine, and dimethylhexylamine; amino groups derived from amines with an aromatic ring, such as 1-(3-aminopropyl)imidazole, pyridin-2-amine, and 3-aminobenzenesulfonic acid; and amino groups derived from compounds to which two or more amino groups are bound via alkyl chains, aromatic compounds, heterocyclic compounds, monocyclic compounds and/or the like (hereinafter referred to as "polyamines"), such as tris(2-aminoethyl)amine, ethylenediamine, diethylenetriamine, triethylenetetramine, tetraethylenepentamine, dipropylenetriamine, polyethylencimine, N-methyl-2,2'-diaminodiethylamine, N-acetylethylenediamine, and 1,2-bis(2-aminoethoxy)ethane. The amino group is preferably an amino group derived from a polyamine, particularly an amino group derived from ethylenediamine, diethylenetriamine, triethylenetetramine, or tetraethylenepentamine, and is more preferably an amino group derived from tetracthylenepentamine. Moreover, the amino group is more preferably an amino group derived from a primary or secondary amine. Furthermore, an amino group with a log P value (P represents an octanol-water partition coefficient) of less than 2.5, such as an amino group derived from tetraethylenepentamine, is suitable for use.

An acidic or basic functional group-containing ligand may be bound to the water-insoluble polymeric material, either directly or via a spacer derived from a reactive functional group (the spacer involved in such binding is also called spacer 2). The spacer 2 can be a spacer with an electrically neutral chemical bond, such as urea bond, amide bond, ether bond, ester bond, or urethane bond, and is preferably a spacer with an amide or urea bond.

Examples of the reactive functional group that mediates the binding between the water-insoluble polymeric material and the ligand include active halogen-containing groups, such as haloacetyl groups, haloacetamidomethyl groups, and halogenated alkyl groups; epoxide group, carboxyl group, isocyanate group, thioisocyanate group, and acid anhydride group. The reactive functional group is preferably an active halogen-containing group, more preferably a haloacetamidomethyl group, because those functional groups have moderate reactivity. Specific examples of a water-insoluble polymeric material with an incorporated reactive functional group include chloroacetamidomethyl group-added polystyrene and chloroacetamidomethyl group-added polysulfone.

The reactive functional group can be bound to a water-insoluble polymeric material by reacting the water-insoluble polymeric material in advance with an appropriate reagent. For example, in cases where the water-insoluble polymeric material is polystyrene and the reactive functional group is chloroacetamidomethyl group, a chloroacetamidomethyl group-bound polystyrene can be obtained by reacting polystyrene with N-methylol-α-chloroacetamide. A polystyrene to which tetraethylenepentamine is bound through the acetamidomethyl group can be obtained, for example, by reacting tetraethylenepentamine having amino groups with chloroacetamidomethyl group-bound polystyrene. In this case, the acetamidomethyl group corresponds to the spacer 2, and the tetraethylenepentamine corresponds to the ligand. Moreover, a polystyrene to which tetraethylenepentamine having a chlorophenyl group via a urea bond is bound through the acetamidomethyl group can be obtained, for example, by reacting tetraethylenepentamine having amino groups with the chloroacetamidomethyl group-bound polystyrene, and additionally reacting chlorophenyl isocyanate with the resultant. Any combination of a material used for the water-insoluble polymeric material, spacers (spacer 1 and spacer 2), and a ligand is available. Examples of a sea component to which a ligand is bound include a polystyrene to which an amino group-containing compound derived from ethylenediamine, diethylenetriamine, triethylenetetramine, or tetraethylenepentamine is bound through an acetamidomethyl group, a polysulfone to which an amino group-containing compound derived from ethylenediamine, diethylenetriamine, triethylenetetramine, or tetraethylenepentamine is bound through an acetamidomethyl group, and a polyether sulfone to which an amino group-containing compound derived from ethylenediamine, diethylenetriamine, triethylenetetramine, or tetraethylenepentamine is bound through an acetamidomethyl group.

The amount of the acidic or basic functional group contained in the ligand is not specifically limited. However, it is believed that a too small amount of the acidic or basic functional group in the ligand results in an insufficient increase of adsorption capacity toward electrically charged sTNFRs in, for example, blood components, and that a too large amount of the acidic or basic functional group in the ligand, on the contrary, leads to an increased hydrophilicity and a decreased strength of the water-insoluble polymeric material. Thus, the amount of an acidic or basic functional group in 1 g of the water-insoluble polymeric material on dry weight basis is, for example, in the range from 0.5 to 5.0 mmol.

The above amount of an acidic or basic functional group can be measured using hydrochloric acid or an aqueous solution of sodium hydroxide by acid-base titration.

Preferably, an acidic or basic functional group-containing ligand is bound to the surface of a water-insoluble polymeric material (specifically, bound to a sea component on the surface of a water-insoluble polymeric material in a form of sea-island type composite fiber) from the viewpoint of increasing the interaction with sTNFRs which are adsorption targets.

The adsorbing material for soluble tumor necrosis factor receptors according to the present embodiment can be used as, for example, a carrier for an adsorption column for use in extracorporeal circulation, a carrier for a column for use in production of blood products, or a carrier for a column for use in separation and purification of sTNFRs. The patient, to whom the above adsorbing material can be applied as a carrier for an adsorption column for use in extracorporeal circulation, is not specifically limited as long as the patient has any disease characterized by a high concentration of free sTNFR1 and/or sTNFR2 in blood, and the adsorbing material can be commonly used for patients such as patients with general inflammation, sepsis, acute respiratory distress syndrome, hepatitis C, cancer, leukemia, atrial fibrillation, heart failure, cachexy, or autoimmune diseases. Among these, examples of the patient include patients with sepsis, acute respiratory distress syndrome, or cancer.

In particular, a material that efficiently adsorbs soluble tumor necrosis factor receptors involved in immunosuppression in cancer patients is expected to improve QoL in cancer patients because immunosuppression is induced in cancer patients by radiation therapy or as a side effect of an anti-cancer drug. The material can be suitably used for treatment of, for example, leukemia, thyroid cancer, liver cancer, kidney cancer, lung cancer, esophagus cancer, stomach cancer, pancreatic cancer, breast cancer, prostate cancer, uterine cancer, cervical cancer, bladder cancer, malignant brain tumor, pharynx cancer, and lymph node cancer, among other cancers.

Additionally, the above adsorbing carrier can hold soluble tumor necrosis factor receptors due to high affinity thereof, and thus separate soluble tumor necrosis factor receptors from other components. After separation from other components, the soluble tumor necrosis factor receptors, which are held by the above adsorbing carrier, can be released from the adsorbing carrier by eluting the adsorbing carrier with a given solution or by soaking the adsorbing carrier in a given solution. A method of allowing the adsorbing carrier to adsorb soluble tumor necrosis factor receptors can be carried out by, for example, producing a material in which the above adsorbing material is packed in syringe-like container, mini-column, or microchip, and then allowing a fluid containing soluble tumor necrosis factor receptors to pass through the adsorbing material or to infiltrate the adsorbing material. A method of releasing soluble tumor necrosis factor receptors from the adsorbing carrier can be carried out by, for example, allowing a solution conditioned to an adequate ion or salt concentration to pass through the adsorbing carrier. Thus, soluble tumor necrosis factor receptors can be obtained in high purity. That is, the adsorbing carrier can also be used as a material for purifying soluble tumor necrosis factor receptors. Also, efficient separation or purification can be achieved by using the adsorbing material in combination with other materials for separation and purification based on ionic properties, hydrophobicity, molecular mass, or pore size.

Additionally, the present invention provides a method of removing soluble tumor necrosis factor receptors using the above adsorbing material.

In one aspect of the method of removing soluble tumor necrosis factor receptors, in which the above adsorbing material is used as a carrier for an adsorption column for use in extracorporeal circulation, the adsorption column can be connected to a blood circuit, which is set in an extracorporeal blood circulation system, to allow a patient's blood to circulate through the circuit for purification of the blood, by which the adsorption column can provide therapeutic benefits. In this method, the adsorption column is applicable to both venous and arterial blood. More specific examples of the above method include a method in which a patient's blood is directly passed through the adsorption column for removal of soluble tumor necrosis factor receptors from the blood (direct blood perfusion therapy), and a method in which a plasma fraction separated from a patient's blood by a plasma separator is passed through the adsorption column for removal of soluble tumor necrosis factor receptors contained in the plasma fraction (plasma perfusion therapy). The blood or the like purified by these methods will be returned to the patient. For patients with renal insufficiency, the adsorption column can be used in combination with an artificial kidney. For patients with pulmonary insufficiency, the adsorption column can also be used in combination with a mechanical ventilator or an extracorporeal membrane oxygenation system.

Additionally, another aspect of the method of removing soluble tumor necrosis factor receptors is a method of using the above adsorbing material to deprive blood products of soluble tumor necrosis factor receptors, which are produced during production of the blood products. In this respect, the term "blood products" refers to various types of blood products for use in blood transfusion, such as whole blood products, red blood cell concentrates, platelet concentrates, albumin products, immunoglobulin products, blood coagulation factor products, or blood coagulation factor-related products. Specifically, soluble tumor necrosis factor receptors contained in, for example, a blood, an intermediate blood product, or a blood product are removed by connecting an adsorption column packed with the above adsorbing material to a tube, a circuit, or a bag for a blood product at any of the steps of producing a blood product from a blood collected during blood donation, and passing, for example, the blood, the intermediate blood product, or the blood product through the adsorption column with a pump or a shaker. Soluble tumor necrosis factor receptors contained in a blood product can also be removed immediately before administration of the blood product to a patient by passing the blood product through an adsorption column packed with the above adsorbing material.

Additionally, the present invention provides an adsorption column comprising the above adsorbing material.

The term "adsorption column" means a column having at least a fluid inlet port, a body case, and a fluid outlet port, in which the body case is packed with the adsorbing material of the invention for soluble tumor necrosis factor receptors (hereinafter referred to also as sTNFR-adsorbing material). Examples of the column include a radial flow column.

Since the adsorption column according to the present embodiment can adsorb sTNFRs from a liquid by passing the liquid through the column, the adsorption column may be used for purification or removal of sTNFRs of interest from a fluid containing the sTNFRs, such as for separating a particular type of sTNFRs, and the like.

A container of any shape can be used for the adsorption column as long as the container has inlet and outlet ports for a liquid containing sTNFRs (hereinafter referred to as liquid) and a body case, in which the body case can be packed with the sTNFR-adsorbing material. Examples of an embodiment include a container that is able to house a pipe wrapped in a cylinder shape with the sTNFR-adsorbing material (hereinafter referred to as cylinder), wherein the liquid flows from the outer periphery of the cylinder to the hollow interior of the cylinder and then flows out of the container, or wherein the liquid flows from the hollow interior of the cylinder to the outer periphery of the cylinder and then flows out of the container. From the viewpoint of production efficiency or of preventing a treatment liquid from taking a shortcut, the cylinder preferably has a structure composed of a pipe with holes on the periphery surface and the sTNFR-adsorbing material wound around the pipe. Specific examples thereof include a radial-flow type container, which comprises a central pipe with holes on the lateral surface in the longitudinal direction to flow out a supplied liquid, a sTNFR-adsorbing material that is packed around the central pipe and adsorbs a target substance contained in the liquid, a plate that is arranged to connect with the central pipe at the upper end in such a manner that the flowing liquid passes through the hollow interior of the central pipe and to prevent the above liquid from contacting with the sTNFR-adsorbing material prior to flowing through the central pipe, and another plate that is arranged to close the central pipe at the lower end and to confine the sTNFR-adsorbing material in a space surrounding the central pipe, wherein the container can be in a cylindrical shape or in a prismatic shape, such as a shape of a triangular prism, a quadrangular prism, a hexagonal prism, or an octagonal prism, but the container is not limited to having the above structure. Moreover, examples of another embodiment include a container with a cylindrical space inside, which space can be filled with disks cut from a sTNFR-adsorbing material, wherein the container has a liquid inlet port and a liquid outlet port. Specific examples thereof include a container with a liquid inlet port and a liquid outlet port, further comprising, inside the container, a plate with a liquid inlet port to flow out a supplied liquid, and another plate with a liquid outlet port to draw out the supplied liquid, and a cylindrical body case packed with disks cut from a sTNFR-adsorbing material. In this case, the shape of the sTNFR-adsorbing material is not limited to a circle but can be appropriately changed to any shape depending on the shape of a container for the adsorption column, including, for example, an ellipse, a polygonal shape such as triangle or square, and a trapezoidal shape.

The container for the adsorption column can be, for example, a glass container, a plastic or resin container, or a stainless steel container, and the size of the container is appropriately selected depending on intended use, and the container for the adsorption column is not specifically limited by, for example, size. However, the container is preferably made from a plastic or resin material and is preferably small enough to be held in hands, and the entire adsorption column preferably has a height of not less than 1 cm and not more than 30 cm, an outer diameter of not less than 1 cm and not more than 10 cm, and an inner volume of not more than 200 $cm^3$, in view of easy operation and easy disposal in clinical and laboratory settings. An adsorption column with a filling volume of 0.94 $cm^3$ (1 cm inner diameter×1.2 cm height, outer diameter: 2 cm) is used in the examples below for reasons of convenience in the analysis, but the adsorption column is not limited thereto.

Preferably, the sTNFR-adsorbing material is laminated and filled in the adsorption column. In this respect, the term "laminate" means that two or more layers of the sTNFR-adsorbing material are piled up in close contact, and examples of the method of laminating and filling the adsorption column include a method in which a plurality of sheets of a sTNFR-adsorbing material processed in sheet form are piled up as seen in the cases of an axial flow column, and a method in which a sTNFR-adsorbing material processed in sheet form is wrapped around a pipe with holes as seen in the cases of radial flow column.

EXAMPLES

The adsorbing material for soluble tumor necrosis factor receptors of the invention will be specifically described below by way of examples. However, the present invention will not be limited by those examples.

(Production of Fiber A)

Polystyrene and polypropylene, which were used as a sea component and an island component, respectively, were individually melted and metered, and were poured into a spinning pack, in which sea-island composite-spinning spinneret nozzles each having 256 holes for dispensing an island component were incorporated, to form a composite flow with a sea-island structure and extrude the melts. The ratio of the island component was adjusted to 50% by weight and the distance from the surface of the water-insoluble polymeric material to the island component at the outermost position was adjusted to 2 µm, to collect the sea-island type composite fiber A with a fiber diameter of 20 µm (hereinafter referred to as Fiber A).

(Production of Fiber B)

Polystyrene and polypropylene, which were used as a sea component and an island component, respectively, were individually melted and metered, and were poured into a spinning pack, in which sea-island composite-spinning spinneret nozzles each having 256 holes for dispensing an island component were incorporated, to form a composite flow with a sea-island structure and to extrude the melts. The ratio of the island component was adjusted to 50% by weight and the distance from the surface of the water-insoluble polymeric material to the island component at the outermost position was adjusted to 2 µm, to collect the sea-island type composite fiber B with a fiber diameter of 30 µm (hereinafter referred to as Fiber B).

(Production of Fiber C)

Polystyrene and polypropylene, which were used as a sea component and an island component, respectively, were individually melted and metered, and were poured into a spinning pack, in which sea-island composite-spinning spinneret nozzles each having 256 holes for dispensing an island component were incorporated, to form a composite flow with a sea-island structure and to extrude the melts. The ratio of the island component was adjusted to 50% by weight and the distance from the surface of the sea-island type composite fiber to the island component at the outermost position was adjusted to 2 μm, to collect the sea-island type composite fiber C with a fiber diameter of 60 μm (hereinafter referred to as Fiber C).

(Production of Fiber D)

Polystyrene and polypropylene, which were used as a sea component and an island component, respectively, were individually melted and metered, and were poured into a spinning pack, in which sea-island composite-spinning spinneret nozzles each having 256 holes for dispensing an island component were incorporated, to form a composite flow with a sea-island structure and to extrude the melts. The ratio of the island component was adjusted to 50% by weight and the distance from the surface of the sea-island type composite fiber to the island component at the outermost position was adjusted to 2 μm, to collect the sea-island type composite fiber D with a liber diameter of 70 μm (hereinafter referred to as Fiber D).

(Production of Non-Woven Fabric E)

According to the method described in the specification of JP 2006-312804 A, a sea-island type composite fiber with 36 islands, in which each island was a core-sheath type composite fiber, was spun using the following components at a spinning rate of 800 m/min and with a draw ratio of 3:

Core component for each island: polypropylene;

Sheath component for each island: kneaded at a ratio of 90% by weight of polystyrene and 10% by weight of polypropylene;

Sea component: a polyester copolymer containing an ethylene terephthalate unit as a main repeat unit and 3% by weight of sodium 5-sulfoisophthalate as a copolymerization component;

Combination ratio (by weight):core:sheath:sea=44:44:12.

The sea-island type composite fiber with 36 islands and a polypropylene with a diameter of 20 μm as an aggregate were mixed uniformly at a ratio of 85:15 by weight, and the resulting mixture was shaped into a sheet. The sheet was subjected to needle punching to obtain a non-woven fabric. Next, this non-woven fabric was treated with an aqueous solution of sodium hydroxide at 90° C. to collect a non-woven fabric E (hereinafter referred to as non-woven fabric F) with the core-sheath fiber having a diameter of 5 μm and with a bulk density of 0.05 g/cm$^3$ (a total weight per area of 250 g/m$^2$).

(Production of Knitted Fabrics A to D)

Cylindrical knitted fabrics A to D (hereinafter referred to as knitted Fabrics A to D) with a weight per area of 0.0039 g/cm$^2$ and a bulk density of 0.22 g/cm$^3$ were produced from the Fibers A to D, respectively, by using a circular knitting machine (MR-1 circular knitting machine; Maruzen Sangyo Co., Ltd.) and adjusting stitch density with a dial.

(Production of Chloroacetamidomethylated Knitted Fabrics)

To a mixed solution of 310 g of nitrobenzene and 310 g of a 98% by weight sulfuric acid solution, 23 g of N-methylol-α-chloroacetamide (hereinafter referred to as NMCA) was added, and the resulting mixture was stirred at 10° C. until the NMCA was dissolved to produce a NMCA solution. Next, 2 g of paraformaldehyde (hereinafter referred to as PFA) was added to a mixture of 20 g of nitrobenzene and 20 g of a 98% by weight sulfuric acid solution, and the resulting mixture was stirred at 20° C. until the PFA was dissolved to produce a PFA solution. To 643 g of the NMCA solution, 42 g of the PFA solution cooled at 5° C. was added, and the resulting mixture was stirred for 5 minutes, and 10 g of the knitted fabric A was later added and soaked in the mixture for 2 hours. Subsequently, the knitted fabric A was immersed in 500 mL of nitrobenzene at a temperature of not higher than 10° C. for quenching, and the resulting knitted fabric was then dipped for 30 minutes in methanol warmed at 40° C. to soak out the attached nitrobenzene, and a chloroacetamidomethylated knitted fabric A was thereby produced. Chloroacetamidomethylated knitted fabrics B to D were individually produced in the same manner as the chloroacetamidomethylated knitted fabric A, except that the knitted fabric A was changed to each of the knitted fabrics B to D.

(Production of Chloroacetamidomethylated Non-Woven Fabric)

In a mixed solution of 600 mL of nitrobenzene and 390 mL of a 98% by weight sulfuric acid solution, 3 g of PFA was dissolved at 20° C. and the resulting solution was then cooled to 0° C. Subsequently, 75.9 g of N-methylol-α-chloroacetamide was added to the solution and dissolved at a temperature of not higher than 5° C., and 5 g of the non-woven fabric E was soaked in the resulting mixture and left at room temperature for 2 hours. Then, the non-woven fabric was taken out from the mixture and immersed in an excess volume of methanol at a temperature of not higher than 10° C. After the immersion in methanol, the non-woven fabric was washed with water and dried to produce a chloroacetamidomethylated non-woven fabric E.

(Production of Tetraethylenepentamine-Para-Chlorophenylated Knitted Fabric)

Tetraethylenepentamine (hereinafter referred to as TEPA) and triethylamine were dissolved in 500 mL of dimethyl sulfoxide (hereinafter referred to as DMSO) to yield concentrations of 5 mM and 473 mM, respectively, and 10 g of the chloroacetamidomethylated knitted fabric B was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetraethylenepentamine-para-chlorophenylated knitted fabric (hereinafter referred to as adsorbing material 1).

(Production of Tetraethylenepentamine-Para-Chlorophenylated Knitted Fabric)

TFPA and triethylamine were dissolved in 500 ml, of DMSO to yield concentrations of 10 mM and 473 mM, respectively, and 10 g of the chloroacetamidomethylated knitted fabric B was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetraethylenepentamine-para-chlorophenylated knitted fabric (hereinafter referred to as adsorbing material 2).

(Production of Tetraethylenepentamine-Para-Chlorophenylated Knitted Fabric)

TEPA and triethylamine were dissolved in 500 mL of DMSO to yield concentrations of 20 mM and 473 mM, respectively, and 10 g of the chloroacetamidomethylated knitted fabric B was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetraethylenepentamine-para-chlorophenylated knitted fabric (hereinafter referred to as adsorbing material 3).

(Production of Tetraethylenepentamine-Para-Chlorophenylated Knitted Fabric)

TEPA and triethylamine were dissolved in 500 mL of DMSO to yield concentrations of 30 mM and 473 mM, respectively, and 10 g of the chloroacetamidomethylated knitted fabric B was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetraethylenepentamine-para-chlorophenylated knitted fabric (hereinafter referred to as adsorbing material 4).

(Production of Tetraethylenepentamine-Para-Chlorophenylated Knitted Fabric)

TEPA and triethylamine were dissolved in 500 mL of DMSO to yield concentrations of 40 mM and 473 mM, respectively, and 10 g of the chloroacetamidomethylated knitted fabric B was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetraethylenepentamine-para-chlorophenylated knitted fabric (hereinafter referred to as adsorbing material 5).

(Production of Tetraethylenepentamine-para-Chlorophenylated Knitted Fabric) TEPA and triethylamine were dissolved in 500 mL of DMSO to yield concentrations of 30 mM and 473 mM, respectively, and 10 g of the chloroacetamidomethylated knitted fabric C was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetracthylenepentamine-para-chlorophenylated knitted fabric (hereinafter referred to as adsorbing material 6).

(Production of Tetraethylenepentamine-Para-Chlorophenylated Knitted Fabric)

TEPA and triethylamine were dissolved in 500 mL of DMSO to yield concentrations of 2.5 mM and 473 mM, respectively, and 10 g of the chloroacetamidomethylated knitted fabric B was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetraethylenepentamine-para-chlorophenylated knitted fabric (hereinafter referred to as adsorbing material 7).

(Production of Tetraethylenepentamine-para-Chlorophenylated Knitted Fabric)

EPA and triethylamine were dissolved in 500 ml, of DMSO to yield concentrations of 50 mM and 473 mM, respectively, and 10 g of the chloroacetamidomethylated knitted fabric B was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetracthylenepentamine-para-chlorophenylated knitted fabric (hereinafter referred to as adsorbing material 8).

(Production of Tetraethylenepentamine-Para-Chlorophenylated Knitted Fabric)

TEPA and triethylamine were dissolved in 500 mL of DMSO to yield concentrations of 30 mM and 473 mM, respectively, and 10 g of the chloroacetamidomethylated knitted fabric A was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetraethylenepentamine-para-chlorophenylated knitted fabric (hereinafter referred to as adsorbing material 9).

(Production of Tetraethylenepentamine-Para-Chlorophenylated Knitted Fabric)

TEPA and triethylamine were dissolved in 500 mL of DMSO to yield concentrations of 30 mM and 473 mM, respectively, and 10 g of the chloroacetamidomethylated knitted fabric D was soaked in the resulting solution at 40° C. for 3 hours to allow a reaction to proceed. The knitted fabric was washed with DMSO three times and then immersed in 500 mL of a 20 mM para-chlorophenyl isocyanate solution in DMSO at 30° C. for 1 hour to allow a reaction to proceed. Subsequently, the knitted fabric was taken out from the reaction solution and dipped and washed with the same volume of DMSO as that of the reaction solution, washed with methanol, and then dipped and washed with water to produce a tetraethylenepentamine-para-chlorophenylated knitted fabric (hereinafter referred to as adsorbing material 10).

(Collection of Particles with Hexadecyl Groups Serving as Ligand)

An adsorption-type blood purification device "Lixelle" (registered trademark; manufactured by Kaneka Corporation), which contains an adsorber composed of cellulose particles with hexadecyl groups as a ligand, was broken to collect the particles filled in a column (hereinafter referred to as adsorbing material 11).

(Production of Dimethyloctylammonium-Functionalized Non-Woven Fabric)

A solution was prepared by dissolving 50 g of N,N-dimethyloctylamine and 8 g of potassium iodide in 360 mL of N,N-dimethylformamide, and 5 g of the chloroacetamidomethylated non-woven fabric E was soaked in the resulting solution and heated in a bath at 85° C. for 3 hours. The non-woven fabric was washed with isopropanol, immersed in a 1 mol/L sodium chloride solution in water, and then washed with water to produce a dimethyloctylammonium-functionalized non-woven fabric (hereinafter referred to as adsorbing material 12).

(Calculation of Peak Radius of Adsorbing Material 1)

About 6 mg of the adsorbing material 1 soaked in water was taken out from the water just prior to DSC analysis, and excess water on the surface was removed off before the adsorbing material 1 was sealed in a sealing-type aluminium sample container. Next, the wet adsorbing material was rapidly cooled down to −55° C. and then heated to 5° C. at a rate of 0.3° C./min using a DSC Q100 (manufactured by TA Instruments, Inc.) for differential scanning calorimetry to obtain a DSC curve, in which the peak top temperatures were melting points. Calibration of temperature and heat flow was achieved using pure water. A pore size distribution curve was generated from the obtained DSC curve according to the method described in Ishikiriyama et al. (Journal of Colloid and Interface Science, 1995, 171: 92-102). In the pore size distribution curve, the pore radius and the pore volume in 1 g of the wet adsorbing material are plotted on the horizontal and vertical axes, respectively. In this respect, the peak radius refers to the pore radius at which the pore volume per weight of a lyophilized adsorbing material reaches the maximum in the pore size distribution curve. The peak radius of the adsorbing material 1 is shown in Table 1.

(Measurement of Zeta Potential of Adsorbing Material 1)

The adsorbing material 1 soaked in water was taken out from the water just prior to zeta potential analysis, and excess water on the surface of the adsorbing material was removed off. The zeta potential analysis was performed using a zeta potential analyzer for solid surface analysis SurPASS™ (manufactured by Anton Paar GmbH). A zeta potential value measured at pH 7.4 and a temperature of 20±5° C. was recorded. The zeta potential of the adsorbing material 1 is shown in Table 1.

(Measurement of Fiber Diameter of Adsorbing Material 1)

The adsorbing material 1 was embedded for cryo-microtome slicing to form a cross section. The obtained observation surface was coated with a conductive material to form an observation sample. Then, the cross section of the observation sample was randomly observed using a field emission scanning electron microscope S-5500 (manufactured by Hitachi High-Technologies Corporation), and 100 cross-sectional images were acquired. The fiber diameter was calculated based on the cross section of a fiber in an obtained cross-sectional image. This procedure was repeated for all of the 100 cross-sectional images, and the average of the calculated diameters was determined as the fiber diameter of the adsorbing material 1. The result is shown in Table 1.

(Calculation of Area Ratio B of Non-Porous Region in Adsorbing Material 1)

The adsorbing material 1 was pretreated by ruthenium tetroxide staining, followed by cryo-ultramicrotomy, and cross sections each passing through the center of the adsorbing material 1 and perpendicular to the longitudinal direction were randomly observed at a magnification of 8,000 times with a transmission electron microscope EM-1400 Plus (manufactured by JEOL Ltd.) at an accelerated voltage of 100 kV, and 100 cross-sectional images were acquired. In the acquired cross-sectional images, the areas of non-porous and porous regions were denoted by A1 and A2, respectively, and the ratio B of the area of the non-porous region was calculated according to the equation (1) below. The areas of the non-porous and porous regions were distinguished based on the porous structure detected in the cross-sectional images. The area of the non-porous region was defined as the sum of the areas of regions where pores with a pore size of less than 10 nm and no pores were observed, while the area of the porous region was defined as the area of a region where pores with a pore size of not less than 10 nm were observed. The areas were calculated using image editing software (Photoshop Elements, 14.0; manufactured by Adobe Inc.). The ratio B of the area of the non-porous region in the adsorbing material 1 is shown in Table 1.

$$B = A1/(A1+A2) \times 100 \qquad \text{Equation (1).}$$

(Calculation of Pore Volume of Adsorbing Material 1)

About 6 mg of the adsorbing material 1 soaked in water was taken out from the water just prior to DSC analysis, and excess water on the surface was removed off before the adsorbing material 1 was sealed in a sealing-type aluminium sample container. Next, the wet adsorbing material was rapidly cooled down to −55° C. and then heated to 5° C. at a rate of 0.3° C./min using a DSC Q100 (manufactured by TA Instruments, Inc.) for differential scanning calorimetry to obtain a DSC curve, in which the peak top temperatures were melting points. Calibration of temperature and heat flow was achieved using pure water. The pore volume of the adsorbing material 1 was calculated from the obtained DSC curve according to the method described in Ishikiriyama et al. (Journal of Colloid and Interface Science, 1995, 171: 92-102). The result is shown in Table 1.

(Calculation of Peak Radius of Adsorbing Materials 2 to 12)

The peak radius in each of the adsorbing materials 2 to 12 was calculated in the same manner as for the adsorbing material 1. The result is shown in Table 1 or 2.

(Measurement of Zeta Potential of Adsorbing Materials 2 to 12)

The zeta potential of each of the adsorbing materials 2 to 12 was calculated in the same manner as for the adsorbing material 1. The result is shown in Table 1 or 2.

(Measurement of Fiber Diameter of Adsorbing Materials 2 to 10 and 12)

The fiber diameter of each of the adsorbing materials 2 to 10 and 12 was calculated in the same manner as for the adsorbing material 1. The result is shown in Table 1 or 2.

(Measurement of Particle Size of Adsorbing Material 11)

The adsorbing material 11 was embedded for cryo-microtome slicing to form a cross section. The obtained observation surface was coated with a conductive material to form an observation sample. Then, the cross section of the observation sample was randomly observed using a field emission scanning electron microscope S-5500 (manufactured by Hitachi High-Technologies Corporation), and 100 cross-sectional images were acquired. The smallest circle that completely enclosed the cross section of a fiber in an obtained cross-sectional image was drawn, and the diameter of the smallest circle was calculated. This procedure was repeated for all of the 100 cross-sectional images, and the average of the calculated diameters was determined as the particle size of the adsorbing material 11. The result is shown in Table 2.

(Calculation of Area Ratio B of Non-Porous Region in Adsorbing Materials 2 to 12)

The area ratio B of the non-porous region in each of the adsorbing materials 2 to 12 was calculated in the same manner as for the adsorbing material 1. The result is shown in Table 1 or 2.

(Calculation of Pore Volume of Adsorbing Materials 2 to 12)

The pore volume of each of the adsorbing materials 2 to 12 was calculated in the same manner as for the adsorbing material 1. The result is shown in Table 1 or 2.

Example 1

1. Evaluation of Adsorption Capacity for Soluble Tumor Necrosis Factor Receptors:

The adsorption rate of soluble tumor necrosis factor receptors was determined in an adsorbing material for soluble tumor necrosis factor receptors by soaking the adsorbing material in a fluid containing soluble tumor necrosis factor receptors for a predetermined period of time, taking out the adsorbing material from the fluid, and measuring the difference in the concentration of soluble tumor necrosis factor receptors in the fluid between before and after soaking. The measurement method is described below. In the method, soluble tumor necrosis factor receptor 1 (sTNFR1) was employed as a potential tumor necrosis factor receptor.

The adsorbing material 1 was cut into disks with a diameter of 6 mm, and eight of the disks were then placed in a polypropylene container. A preparation of soluble tumor necrosis factor receptor 1 (recombinant human TNFRI/TNFRSF1A, 636-RI; R&D Systems®, Inc.) in fetal bovine serum (hereinafter referred to as FBS) at a concentration of 10,000 pg/mL was added to the container at a rate of 1 mL per 0.055 cm$^3$ of the adsorbing material 1, shaken by inversion for 2 hours in an incubator at 37° C., and then analyzed by enzyme-linked immunosorbent assay (ELISA: with Human TNF R1/INFRSF1A Quantikine® ELISA Immunoassay kit, DRT100; R&D Systems®. Inc.) to measure the concentration of sTNFR1 in the FBS. The adsorption rate of sTNFR1 was calculated from the concentrations of sTNFR1 before and after the inversion by the following equation (2). The result is shown in Table 1.

Adsorption rate of sTNFR1 in the adsorbing material 1(%)=[sTNFR1 concentration before inversion (pg/mL)−sTNFR1 concentration after inversion (pg/mL)]/sTNFR1 concentration before inversion (pg/mL)×100   Equation (2)

2. Evaluation of Adsorption Capacity for Platelet:

The adsorption rate of platelet was determined by allowing blood from healthy human volunteers to pass through a mini-column packed with the adsorbing material 1 and then measuring the difference in the platelet count in the blood between before and after passing through the mini-column. The measurement method is described below.

Disks with a diameter of 1 cm were cut from the adsorbing material 1 and a cylindrical column (1 cm inner diameter×1.2 cm height, filling volume: 0.94 cm$^3$, outer diameter: 2 cm; made from polycarbonate) with fluid ports at the upper and lower ends was filled with a stack of the disks to produce a column packed with the adsorbing material 1. While blood from healthy human volunteers (0.13 mg of nafamostat mesilate was added to 1 mL of blood for blood collection) supplemented with LPS at 70 EU/mL was shaken at 65 rpm for 30 minutes in a water bath at 37° C., the blood was pumped through the column at a flow rate of 0.63 mL/min, and blood samples were collected at either the inlet or outlet port of the column. As the sample from the inlet port of the column, a sample was collected from the blood soaked in the water bath (the blood before transferred into the column). As the sample from the outlet port of the column, a sample was collected from the blood at any time from 3.5 to 6.5 minutes after blood transfer into the column (the blood transferred into the column), where the starting time point of blood transfer into the column was designated as 0 minutes. An automated hematology analyzer XT-1800i (manufactured by Sysmex Corporation) was used to measure the platelet count in each of the collected blood samples. Then, the adsorption rate of platelet was calculated by the following equation (3). The result is shown in Table 1.

Adsorption rate of platelet (%)=(Platelet count before transfer into the column−Platelet count after transfer into the column)/Platelet count before transfer into the column×100   Equation (3)

Example 2

The adsorption rate of sTNFR1 and the adsorption rate of platelet were measured using the adsorbing material 2 in the same manner as Example 1. The result is shown in Table 1.

Example 3

The adsorption rate of sTNFR1 and the adsorption rate of platelet were measured using the adsorbing material 3 in the same manner as Example 1. The result is shown in Table 1.

Example 4

The adsorption rate of sTNFR1 and the adsorption rate of platelet were measured using the adsorbing material 4 in the same manner as Example 1. The result is shown in Table 1.

Example 5

The adsorption rate of sTNFR1 and the adsorption rate of platelet were measured using the adsorbing material 5 in the same manner as Example 1. The result is shown in Table 1.

Example 6

The adsorption rate of sTNFR1 and the adsorption rate of platelet were measured using the adsorbing material 6 in the same manner as Example 1. The result is shown in Table 1.

Comparative Example 1

The adsorption rate of sTNFR1 and the adsorption rate of platelet were measured using the adsorbing material 7 in the same manner as Example 1. The result is shown in Table 2.

Comparative Example 2

The adsorption rate of sTNFR1 and the adsorption rate of platelet were measured using the adsorbing material 8 in the same manner as Example 1. The result is shown in Table 2.

Comparative Example 3

The adsorption rate of sTNFR1 and the adsorption rate of platelet were measured using the adsorbing material 9 in the same manner as Example 1. The result is shown in Table 2.

(Comparative Example 4)

The adsorption rate of sTNFR1 and the adsorption rate of platelet were measured using the adsorbing material 10 in the same manner as Example 1. The result is shown in Table 2.

Comparative Example 5

The adsorption rate of sTNFR1 and the adsorption rate of platelet were measured using the adsorbing material 11 in the same manner as Example 1. The result is shown in Table 2.

Comparative Example 6

The adsorption rate of sTNFR1 and the adsorption rate of platelet were measured using the adsorbing material 12 in the same manner as Example 1. The result is shown in Table 2.

TABLE 1

| | | Examples | | | | | |
| --- | --- | --- | --- | --- | --- | --- | --- |
| Evaluation items | Unit | 1 Adsorbing material 1 | 2 Adsorbing material 2 | 3 Adsorbing material 3 | 4 Adsorbing material 4 | 5 Adsorbing material 5 | 6 Adsorbing material 6 |
| Peak radius | nm | 1 | 2 | 4.3 | 16.2 | 47 | 80 |
| Zeta potential | mV | −9.8 | −5.2 | 0.2 | 8.9 | 14.5 | 10.4 |
| Fiber diameter or pore size | μm | 30 | 30 | 30 | 30 | 30 | 60 |
| Area ratio B of non-porous region | % | 50 | 50 | 50 | 50 | 50 | 10 |
| Pore volume | cm$^3$/g | 0.31 | 0.42 | 0.92 | 1.2 | 0.21 | 0.06 |
| Adsorption rate of sTNFR1 | % | 68 | 78 | 89 | 83 | 53 | 52 |
| Ratio of platelet adsorption | % | 77 | 31 | 33 | 36 | 38 | 24 |

In Table 1, the row "Peak radius" represents the peak radius calculated from a distribution of melting points measured by differential scanning calorimeter, and the row "Zeta potential" represents the zeta potential at pH 7.4, and the row "Area ratio B of non-porous region" represents the area ratio of a non-porous region defined by the equation (1), where the areas of non-porous and porous regions are denoted by A1 and A2, respectively, in a cross section passing through the center of an insoluble polymeric material and perpendicular to the longitudinal direction, and the row "Pore volume" represents the pore volume calculated from a distribution of melting points measured by differential scanning calorimeter, and the row "Adsorption rate of sTNFR1" represents the adsorption rate of soluble tumor necrosis factor receptor 1 (sTNFR1).

TABLE 2

| | | Comparative Examples | | | | | |
| --- | --- | --- | --- | --- | --- | --- | --- |
| Evaluation items | Unit | 1 Adsorbing material 7 | 2 Adsorbing material 8 | 3 Adsorbing material 9 | 4 Adsorbing material 10 | 5 Adsorbing material 11 | 6 Adsorbing material 12 |
| Peak radius | nm | 0.5 | 96 | 82 | 88 | 0.8 | 81.3 |
| Zeta potential | mV | −19.0 | 26.0 | 10.2 | 10.4 | −5.1 | 0.3 |

TABLE 2-continued

| Evaluation items | Unit | Comparative Examples | | | | | |
|---|---|---|---|---|---|---|---|
| | | 1 Adsorbing material 7 | 2 Adsorbing material 8 | 3 Adsorbing material 9 | 4 Adsorbing material 10 | 5 Adsorbing material 11 | 6 Adsorbing material 12 |
| Fiber diameter or pore size | μm | 30 | 30 | 20 | 70 | 460 | 5 |
| Area ratio B of non-porous region | % | 50 | 50 | 50 | 50 | 5 | 5 |
| Pore volume | cm³/g | 0.03 | 0.04 | 0.05 | 0.05 | 0.05 | 0.05 |
| Adsorption rate of sTNFR1 | % | 35 | 14 | 92 | 34 | 40 | 23 |
| Ratio of platelet adsorption | % | 19 | 27 | 82 | 18 | 60 | 85 |

The evaluation items in Table 2 are the same as those in Table 1.

The results in Tables 1 and 2 indicated that the adsorbing materials of the invention had excellent adsorption capacity for the soluble tumor necrosis factor receptor, and also indicated that the adsorbing materials of the invention had a moderately reduced adsorption capacity for platelet, which plays a useful role in maintaining biological hemostasis.

INDUSTRIAL APPLICABILITY

An adsorbing material according to the present invention can efficiently adsorb soluble tumor necrosis factor receptors and therefore may be used in medical applications for treatment of biological components, particularly treatment of blood components.

LIST OF REFERENCE NUMERALS

1: Maximum pore volume
2: Peak radius
3: Water-insoluble polymeric material in fiber form
4: Center
5: Sign denoting the direction perpendicular to the longitudinal direction
6: Cross section passing through the center and perpendicular to the longitudinal direction
7: Lines passing through the center on the cross section perpendicular to the longitudinal direction
8: Water-insoluble polymeric material in spherical particle form
9: Water-insoluble polymeric material in ellipsoidal particle form
10: Water-insoluble polymeric material in film form
11: Porous region
12: Non-porous region

The invention claimed is:

1. An adsorbing material for soluble tumor necrosis factor receptors, comprising a superficially porous water-insoluble polymeric material, wherein the pore size distribution curve for the surface of the water-insoluble polymeric material, which is derived from a distribution of melting points determined by differential scanning calorimeter, shows the peak radius in the range of 1 to 80 nm;

the water-insoluble polymeric material has a zeta potential at pH 7.4 of −15 to 15 mV; and the water-insoluble polymeric material is in fiber, particle, or film form.

2. The adsorbing material according to claim 1, wherein the water-insoluble polymeric material is in fiber form with a fiber diameter of 25 to 65 μm or in particle form with a particle size of 25 to 65 μm.

3. The adsorbing material according to claim 1, wherein the ratio B defined by the following equation (1) is not less than 10% and not more than 90%, where A1 and A2 represent the areas of non-porous and porous regions, respectively, in a cross section passing through the center of the water-insoluble polymeric material and perpendicular to the longitudinal direction, and B represents the ratio of the area of the non-porous region:

$$B = A1/(A1+A2) \times 100 \qquad \text{Equation (1)}.$$

4. The adsorbing material according to claim 1, wherein the peak radius is in the range of 1 to 30 nm.

5. The adsorbing material according to claim 1, wherein the water-insoluble polymeric material has a pore volume of 0.6 to 1.2 cm³/g.

6. The adsorbing material according to claim 1, wherein an amino group-containing ligand is bound to the surface of the water-insoluble polymeric material.

7. The adsorbing material according to claim 1, wherein the water-insoluble polymeric material contains polystyrene, polyethylene, or polypropylene as a main component.

8. An adsorption column comprising the adsorbing material according to claim 1.

* * * * *